United States Patent [19]

Mumford

[11] Patent Number: 5,420,653

[45] Date of Patent: May 30, 1995

[54] METHOD AND APPARATUS FOR THE AMELIORATION OF VISUAL STRESS AND DYSLEXIA

[76] Inventor: Robin B. Mumford, 29 S. Bay Ave., Highlands, N.J. 07732

[21] Appl. No.: 817,099

[22] Filed: Jan. 6, 1992

[51] Int. Cl.⁶ .......................... A61B 3/00; A61B 3/02
[52] U.S. Cl. ..................... 351/246; 351/200; 351/239
[58] Field of Search ................ 351/200–203, 351/222, 223, 237, 239–244, 246; 128/741–748

[56] References Cited

U.S. PATENT DOCUMENTS

| | | | |
|---|---|---|---|
| 3,906,644 | 9/1975 | Levinson et al. | 434/184 |
| 3,940,485 | 2/1976 | Levinson et al. | 514/255 |
| 3,952,728 | 4/1976 | Levinson et al. | 128/630 |
| 4,007,273 | 2/1977 | Levinson et al. | 514/226.2 |
| 4,435,052 | 3/1984 | Guyton | 351/239 |
| 4,706,686 | 11/1987 | Levinson | 128/745 |
| 4,764,973 | 8/1988 | O'Hair | 382/14 |
| 4,838,681 | 6/1989 | Pavlidis | 351/210 |
| 4,854,695 | 8/1989 | Lewis | 351/239 |
| 4,869,589 | 9/1989 | Blair et al. | 351/244 |
| 4,889,422 | 12/1989 | Pavlidis | 351/210 |
| 4,961,640 | 10/1990 | Irien | 351/44 |
| 4,979,812 | 12/1990 | Reese | 351/246 |
| 4,979,902 | 12/1990 | Morelle et al. | 434/184 |

Primary Examiner—Loha Ben
Assistant Examiner—Thong Nguyen
Attorney, Agent, or Firm—Robert M. Skolnik

[57] ABSTRACT

A quantitative visual test measures the rate at which an individual is able to complete a defined visual task, either on paper or on a self illuminated screen. The task involves comparing a plurality of similar appearing numbers to determine if they are an exact match within predetermined levels of time. Inability to complete the test within the predetermined level of time indicates the likelihood that the individual will exhibit visual stress and dyslexia. Individuals under such stress are then remediated by the use of adjusted lighting environments sometimes including other visual aids.

18 Claims, 3 Drawing Sheets

FIG. 1

NUMBER PAIRING

ARE THE NUMBERS IN THE PAIRS THE SAME OR DIFFERENT

| 135 | 135 30 | 9786 | 9876 | 44 1427589 | 142589 46 |
|---|---|---|---|---|---|
| 4127 | 4217 34 | 40 10716 | 10617 42 | 1106 | 1016 |
| 92 | 62 38 | 81547 | 85147 | 753168 | 753138 |
| 781 | 718 | 27891 | 2788 | 8463421 | 8462421 |
| 9183 | 9163 | 36479 | 36479 | 974532 | 975432 |
| 14781 | 14718 | 981235 | 981235 | 153689 | 156389 |
| 53918 | 53918 | 76451 | 76541 | 8135427 | 8125437 |
| 1954 | 1946 | 81257 | 81527 | | |

LOOK AT AND POINT TO EACH PAIR OF NUMBERS AND SAY "SAME" OR "DIFFERENT"

LOOK AT THE ROW OF 0'S AND SEE IF THEY APPEAR TO BE JOINED TOGETHER YES/NO

METHOD AND APPARATUS FOR THE AMELIORATION OF VISUAL STRESS AND DYSLEXIA

BACKGROUND OF THE INVENTION

The term dyslexia is used in the context of this disclosure to describe an individual who persistently reads inaccurately and one who has a lower than average recall or comprehension of the contents of what the individual has recently read. In some cases, the individuals are unable to count more than five symbols due to the level of visual confusion. This condition creates a great deal of frustration for such individuals, and is frequently incorrectly perceived as a lack of intelligence. Accordingly, there is a continuing need for and interest in improved methods for the detection and treatment of this and other similar visual conditions.

DESCRIPTION OF THE PRIOR ART

The prior art discloses various different vision tests and screening methods. These tests typically define an individual's ability to read known letters or numbers of different sizes at various distances. The 100 year old Snellen test, which is an example of this type of test, reports an acuity such as 20/10 or 20/20 etc., reflecting the ratio of the distance at which the letters are recognized by a particular individual compared with the standard 20 feet.

Screening systems such as the one practiced utilizing the testing machine known by the trademark TITMUS, and other similar systems, attempt to measure the ability of an individual to see gaps which are rotated in successive images viewed by the individual under test. Such tests detect abnormalities in vision, for instance astigmatism or lack of focus.

Still other screening systems, such as the one known under the trademark Eyedex, causes the eyes of an individual to view the same object as two separate images, allowing the eye muscles to relax. From this test, the extent to which normal fusion of an image by the two eyes is a source of eye muscle stress to the individual can be determined.

Other known tests involve the selection of colored filters to enable an individual, while reading, to optimize their comfort level by selection of their preferred tint. This test is targeted particularly towards the so-called learning disabled individual.

Tests utilizing grids of graduated contrast printed lines have been employed to determine contrast sensitivity of individuals.

The test of the present invention described hereinafter was developed in response to the need to have a quantitative and portable on-site test of the individuals in their particular work environments. There are believed to be many more sources of visual work than presently defined, and accordingly a need for a testing method which provides a quantitative measurement of visual capacity within a time frame, allowing for the comparison of different optical environments and their impact on an individual.

SUMMARY OF THE INVENTION

The present invention discloses a test which quantitatively measures an individual's visual capacity for reading and similar scanning activities utilizing test charts on printed paper or on a video terminal. A first test chart includes a plurality of pairs of identical or similar numbers disposed in parallel columns. An individual's visual capacity is measured in accordance with their ability and time taken to correctly identify whether the numbers in each pair are the same or different. A second test chart includes a plurality of rows of closely spaced "o's", with the number of "o's" in each row increasing with the vertical position of the row on the chart. An individual's visual capacity is measured in accordance with their ability and time taken to count the number of "o's" in each row. The test also provides for the measurement of an individual's visual capacity for reading and optimizing non-paper media such as video terminals. The method of the present invention allows the adjustment of video display terminals to maximize an individual's work capacity with different configurations of the screen.

The present invention relieves dyslexia and other visual incapacities by testing methods combined with empirical optimization of the spectrum of the lighting and the ratio of direct to indirect lighting to achieve optimal visual capacity levels.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 1 is a plan view illustrating a test sheet, or test video screen, for use in a timed number comparison test in accordance with the method of the present invention.

FIG. 2 is a plan view illustrating a test sheet, or test video screen, for use in an image separation ability test in accordance with the method of the present invention.

DETAILED DESCRIPTION OF THE PREFERRED EMBODIMENT(S)

Figure 3:
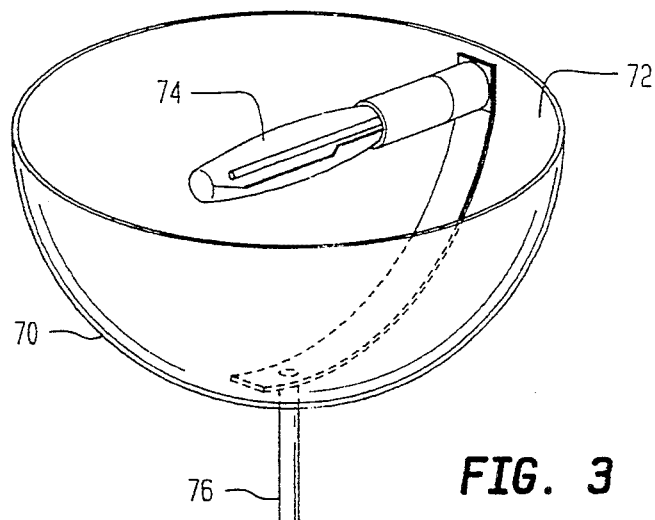
FIG. 3 is a perspective view illustrating a first alternative high intensity discharge lighting source possessing particular spectral and other light distribution features for use in conjunction with the visual tests according to the method of the present invention.

Referring now to the drawings, wherein like reference numerals designate corresponding structure throughout the views, and referring in particular to FIG. 1, a timed number comparison test sheet 10 may be formed by printing on a paper sheet 11, or by causing a similar display on a video terminal. The test sheet 10 includes instructional indicia 12 and 14 which inform the individual being tested of the operations to be performed. A plurality of horizontally spaced, vertically aligned pairs of multi-digit numbers are arranged in parallel columns 16, 18, 20, 22, 24 and 26. The numbers are preferably printed using 6 point helvetica font numbers. At an observation distance of eighteen inches the acuity corresponds to less than 20/30 for the test, utilizing the 6 point numbers. For a typical video terminal screen employing numbers 0.3 inches high, the acuity requirements are less than 20/60 at an observation distance of two and a half feet. The various number pairs on the test sheet 10 have various different relationships. For example, the number pair designated by reference numerals 28 and 30 consists of identical digits "135". The number pair 32, 34 consists, respectively of digits "4127" and "4217", and one of the numbers can accordingly be derived by transposing two of the digits of the other number. The number pair 36, 38 consists, respectively of digits "92" and "62". Thus, one of the numbers can be derived by inverting one of the digits in the other number. The number pair 40, 42 consists, respectively of digits "10716" and "10617", and one of the numbers can be derived by swapping or exchanging the positions of the central and right-end digits of the other number. The number pair 44, 46 consists of the digits "1427589" and "142589". One of the numbers can be derived by adding (or deleting) the "7" digit from the other number. The number pair 48, 50 consists of the digits "8135427" and "8125437". As a result, one of the numbers can be derived from the other by changing the third digit from a "3" to a "2", and vice versa. As may now be readily understood, the test sheet 10 is comprised of a plurality of pairs of numbers, in which the numbers in each pair are either the same, or quite similar. The similar number pairs can be formed by transposing one or more pairs of digits, by inverting symmetrical digits (i.e. 6, 9), by exchanging the positions of one or more digits, by adding one or more digits, or by deleting one or more digits. The test requires an individual to focus on a particular number pair, and to coordinate eye and mind to conduct a comparison.

The test sheet 52 of FIG. 2 may be printed on a paper sheet 53, or alternatively formed by a display on a conventional video terminal. The test sheet 52 includes instructional indicia 54, 56, 58, which inform an individual being tested of the operations to be performed. The test sheet 52 includes five vertically spaced rows 60, 62, 64, 66, 68, each formed by a series of 6 point helvetica font small case "o's", each possessing a diameter of 0.045 inches and separated by spaces of 0.006 inches from adjacent "o's". The number of "o's" in each row increases with the vertical position of the row on the sheet 52. Accordingly, it will be quite easy for an individual to determine that there is only one "o" in row 68. As the individual progresses upwardly, it will become increasingly difficult to count the "o's" in each row, depending upon the separation between the "o's" perceived by the particular individual. If the "o's" appear separated, the individual will be able to count the row 62 of seven "o's" without difficulty.

FIG. 3 shows a configuration of a first alternative lighting fixture required for the indirect lighting part of the test. It is arranged so that the source of light is as high as possible relative to the diffuser so as to maximize the light available to the ceiling. The fixture includes a hemispherical diffuser 70 formed from a translucent material and having an open upper end 72. The diffuser allows from 10%–30% of the light to be transmitted and the rest to be absorbed or reflected. The diffuser is typically made from molded natural unpigmented polypropylene which is translucent and diffuses light. Similar effects may be obtained using nylon or polyethylene. The diffuser was obtained from Fantasy Lighting Company. A high intensity discharge lamp 74 is mounted diametrically across the diffuser 70, adjacent to the upper end 72. The lamp 74 is of a type providing an elongated pencil-shaped light source, which is oriented in the transverse equatorial plane within the diffuser 70. The fixture may be supported on a conventional floor stand by a vertical standard 76, or may alternatively be suspended from a room ceiling by suitable fasteners.

Figure 4:
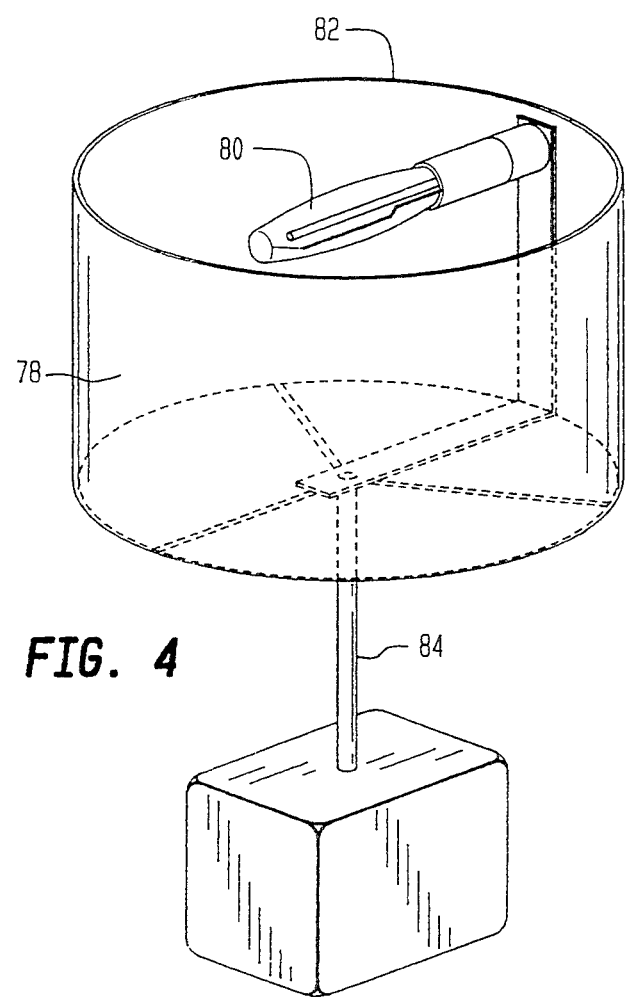
FIG. 4, is a perspective view illustrating a second high intensity discharge lighting source possessing an alternative diffuser for use in conjunction with the visual tests according to the method of the present invention.

FIG. 4 depicts a second alternative lighting fixture for use in the indirect lighting portion of the test. The fixture includes a cylindrical diffuser 78 formed from a translucent material and having open upper and lower circular ends. A high intensity discharge lamp 80 is mounted diametrically across the diffuser 78, adjacent the upper end 82. The lamp 80 is of the type providing an elongated pencil-shaped light source, which is oriented in a transverse plane within the diffuser 78. The fixture may be supported on a conventional floor stand by a vertical standard 84, or may alternatively be suspended from a room ceiling by suitable fasteners.

Figure 5:
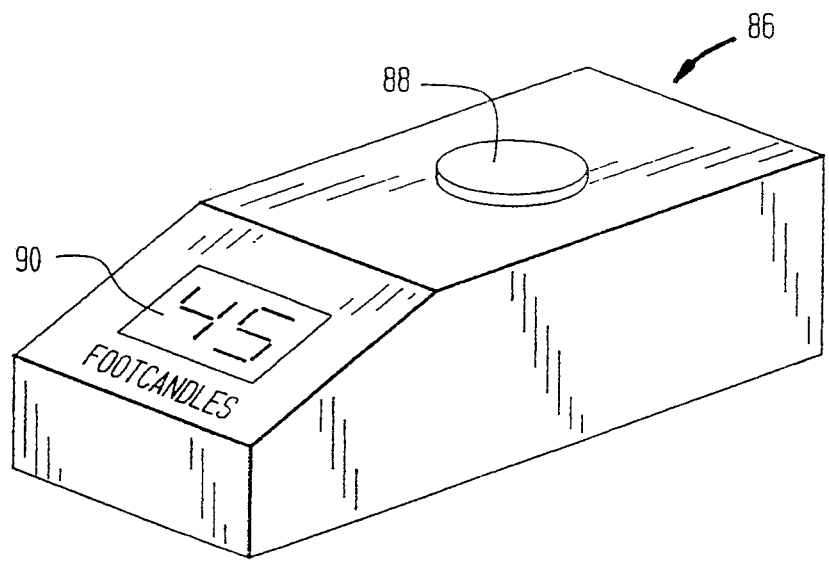
FIG. 5 is a perspective view depicting a conventional light meter for use in measuring light levels in conjunction with the method of the present invention.

FIG. 5 illustrates a conventional digital light meter 86 utilized to estimate the proportion of indirect versus direct light. The light meter includes a sensor 88 and a digital display 90. A suitable light meter is marketed under the trademark GTE SYLVANIA Light Meter Model 2000.

As shown in FIG. 5, the light meter 86 may be configured to measure indirect lighting by supporting an opaque screen 92 above the sensor 88 upon small diameter legs 94. The screen 92 is preferably circular with a diameter twice that of the sensor 88, and is preferably disposed 1.5 inches vertically above the sensor 88. The screen 92 prevents direct light shining in a vertically downwardly direction from impinging on the sensor 88. Thus, the only light measured by the meter 86 will be light reflected from the walls, ceiling, floor and furnishings of the room. By first measuring all room light by employing the light meter 86 without a screen as shown in FIG. 5, and subsequently measuring reflected light utilizing the meter in conjunction with the screen 92, a ratio of direct to reflected light can be obtained.

In the method according to the present invention, testing is first conducted in a room environment with fluorescent lighting of the daylight type in a direct and diffusing mode and at a level of 25 to 100 foot candles measured where the test paper is positioned. An individual to be tested is provided with the test chart of FIG. 1, shown the pairs of numbers and asked to say out loud, whether each pair of numbers are the same or different. The response time is measured and an answer in seconds is determined. Immediately following this test, the individual is shown the test chart illustrated in FIG. 2 and asked whether the "o's" appear to be individual (spaced) or joined together. The individual is then asked to count the "o's" in a selected row.

Generally, a time of over 45 seconds to complete the test chart shown in FIG. 1 and/or an appearance of the "o's" of the test chart shown in FIG. 2 being joined, or a difficulty in counting the number of "o's" in a row, is a sign of some abnormality or lack of appropriate correction.

Figure 6:
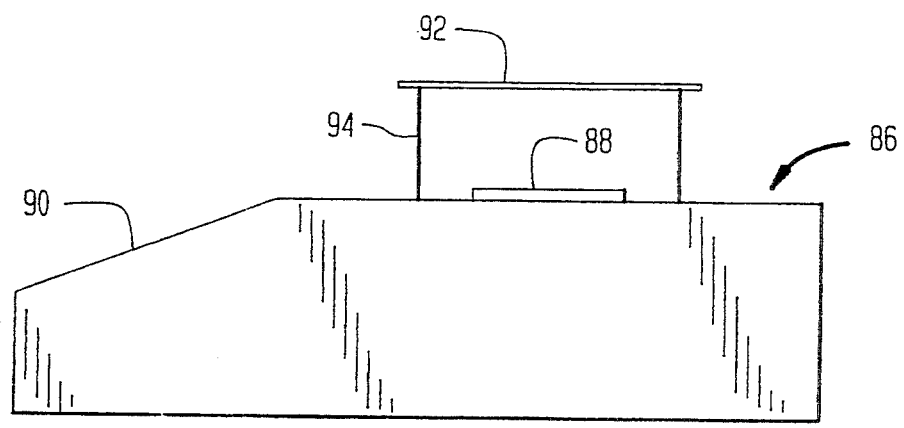
FIG. 6 is a side elevational view illustrating the light meter of FIG. 5 employed in conjunction with an opaque screen so as to measure only indirect light to allow determination of the proportion of indirect vs. direct light.

After completion of the testing utilizing the test charts of FIGS. 1 and 2 under daylight fluorescent lighting conditions and an identification of any visual capacity problems, the room environment is modified to provide a second type of lighting which may be at the same level of foot candles, but of indirect form such that at least 50% of the light is contributed from the lighted ceiling and the balance may be up to 25% laterally reflected from walls and up to a further 25% diffused by a shade or neutral filter. The filter is preferably of cylindrical (FIG. 4) or hemispherical shape (FIG. 3). The relative amount of indirect light present is confirmed with a light meter by interposing an opaque object twice the diameter of the sensing area one and one half inches away in the direction of the source of the light (FIG. 6). The room lighting is adjusted until less than 50% of the light is direct.

The spectra of the light is preferably restricted such that over 50% of the light is provided by three to five principal colors such as produced by high intensity discharge lamps and by fluorescent systems modified to achieve spectral concentration. The preferred high intensity discharge lamps are for instance commercially available from G. E., Philips Lighting and Osram and Others and sold generally as High Pressure Sodium Lamps (70 watts, 100 watts, 150 watts, 250 watts, 400 watts, and 1,000 watts are the most common wattages used) and the description describes those with improved color rendition and also the earlier types. A color temperature of the lamp of 2500 to 2700 degrees is preferred for normal high intense visual activities although color temperatures approaching noon sunlight at 5500 degrees may also be used for special effects.

The next step is to determine the correction and lighting environment of benefit to the individual being tested perceive the "o's" of the test chart shown in FIG. 2 as being separate. Where the individual reports that the "o's" appear joined, generally, color filters under fluorescent lighting will provide a general preference in most cases for one particular color group. This might be a blue or a green or a yellow for instance. Such filters are available commercially from the Irlen Clinic in New York and also as filters for theatrical lighting made by Lee Colortran International. The color effects are achieved by printing plain clear plastic sheets of plastic, such as polyester, or by the addition of color, either transparent or translucent, to the plastic before it is made into a sheet. Each sheet is different in its effect upon individual's specific visual reaction. The individual then examines the "o's" under low UV content predominantly indirect lighting of low glare and restricted spectral diversity and preferably with a color temperature not exceeding 2800 degrees. Color Temperature of lighting is defined as the temperature at which a heated iron bar most nearly matches the lighting under test.

The "o's" can appear to aggregate from two distinct causes. A lack of focus will make the images fuzzy for instance, and the images will appear blurred and fused but stationary. If the images do not stay motionless, they will appear to overlap. The objective of the test is to determine the circumstances under which the images appear clear, separated, and motionless.

This requires correcting any problem of simple focus or astigmatism or eye muscle balance by appropriate prescription lenses and then providing the appropriate filters and lighting. At this stage the individual can read with normal speed and accuracy and will gain in speed of reading and scanning ability over the ensuing months with practice. Once this new enhanced visual capacity has been achieved, a reduced dependency on the different forms of correction is usually encountered and an improvement in basic reading comprehension becomes evident.

In accordance with the method of the present invention, video terminal efficiency is determined by a timed test of how long an individual takes to do the timed numbers test of FIG. 1 when the numbers are on the video terminal screen. If the paper form of the test shown in FIG. 1 takes 40 seconds, for instance, and the video terminal form of the same test takes 48 seconds, the efficiency is 40/48 or 82%. The efficiency will vary with each individual and also with the screen configuration in terms of color, lack of motion and character image form as seen by the individual. To adjust the video terminal character display parameters, the first adjustment of the terminal characters is the choice of foreground and background colors. From the brightest or most severe contrast of green on black to the softer yellow on blue to the conventional black on white, the individual will find their own preference. Next the brightness is adjusted, preferably using a smoke acrylic filter available commercially as acrylic sheet from Rohm and Haas or DuPont for instance. The filter serves to reduce the contrast within the color combination already selected and to reduce the gradient presented to the eye in moving from a white piece of paper on a desk to a self illuminated screen in the form of the video terminal. Included in this optimization is the use of lighting with the spectra and distribution appropriate to the task. These steps provide the means whereby the video terminal can be optimized for a particular individual, to increase job performance and reduce visual stress.

The following case histories illustrate successful applications of the method of the present invention to help individual's overcome various visual incapacities and dyslexia.

Case History 1. A 50 year old dyslexic male could read only with difficulty and low retention under conventional cool white fluorescent lighting at a level of 50 footcandles. The matched numbers test took 65 seconds to achieve on the first attempt. Further studies elicited a preference for a green filter corresponding to Lee Colortran 242 with his reading glasses (+1.75 OD and OS). Using the light fixture of the general design shown in FIG. 4, with a 40 watts incandescent light as well as a 70 watts high pressure sodium lamp GE Lucalox controlled by an Advance Transformer electro magnetic ballast, the individual reported an immediate marked reduction in fatigue and the ability to work longer hours without fatigue. The light level of the principally indirect light was 40 foot candles. Over the course of the next several months, the subject was able to achieve scanning reading of reports, not possible before. This new skill survived the loss of his glasses six months later. At this time and without tints, the individual can scan read without the special tints and can now read normally in formerly hostile environments such as cool white conventional fluorescent lighting.

Case History 2. An 18 year old dyslexic male High School Student was 20/20 but unable to achieve normal reading levels and accuracy. After testing with tints, a peach colored Irlen tint was found which improved reading skills to normal levels. The individual's acuity improved to 20/10 after conventional correction. A preference for the lighting of the type in Case History 1 was expressed and after this the student was able to study normally. The tints and lighting provided complementary gains in this example and both continue in use.

Case History 3. A 17 year old dyslexic High School Junior girl was able to achieve only an error rate of three per paragraph under normal cool white fluorescent lighting at 50 footcandles. The time to complete the matching numbers test was 65 seconds and the individual was unable to count up the row of 7 "o's" due to the confusion and fatigue caused by the numbers test. The "o's" appeared joined together. A green filter similar to example 1 was found to provide the most relief among ten tried. When the lighting was changed to a fixture of the type shown in FIG. 3, using 250 watts High Pressure Sodium GE Lucalox 250 DX powered by an electro magnetic ballast from Advance Transformer, in combination with the filter, normal speed and accuracy of reading was immediately restored.

Case History 4. A 40 year old teacher was able to complete the number matching test in 50 seconds but found the test "o's" to be joined together under conventional cool white fluorescent lighting. Upon changing to a lighting system described in Case History three, the "o's" separated indicating an improved acuity. In this case no filter was required since vision was remediated merely by a change in the lighting.

Case History 5. Eight librarians in a business library were tested using the number test on paper and the results were compared with those from doing the same test using the same numbers on a video screen a few minutes later. The screen was optimized for each individual as described previously. The average loss of efficiency was 17% in moving from the paper to the video terminal. The paper test was done in the office of each individual which was lit by fixtures of the type in FIG. 3 except that the lamps were 70 watts High Pressure Sodium of the GE Lucalox type and powered by Advance Transformer Ballasts. The terminal test was done under ambient cool white fluorescent lighting.

All of the individuals of case histories 1-5 above reported a reduction in fatigue as a result of lowering the work content of their activities when using the lighting disclosed in this invention.

It is to be understood, however, that even though numerous characteristics and advantages of the present invention have been set forth in the foregoing description, together with details of the structure and function of the invention, the disclosure is illustrative only, and changes may be made in detail, especially in matters of materials, shape, size and arrangement of parts within the principles of the invention to the full extent indicated by the broad general meaning of the terms in which the appended claims are expressed.

What is claimed is:

1. A method for measuring visual capacity of an individual comprising the steps of: providing a test chart including a plurality of adjacent pairs of multi-digit numbers, with some of said number pairs being the same and others of said number pairs being similar;
   positioning an individual at a predetermined observation distance from said test chart;
   instructing said individual to compare each number pair on said test chart to determine whether they are the same;
   recording an accuracy with which said individual compares the number pairs on said test chart;
   recording a time taken by said individual to compare all number pairs on said test chart; and
   comparing the accuracy and time taken by the individual with predetermined standards for accuracy and time.

2. The method of claim 1, wherein said number pairs are formed by a plurality of pairs of adjacent number columns.

3. The method of claim 1, wherein at least one of said similar number pairs includes a first number and a second number, and wherein said first number can be converted into said second number by transposing two adjacent digits.

4. The method of claim 1, wherein at least one of said similar number pairs includes a first number and a second number, and wherein said first number can be converted into said second number by inverting one or more digits.

5. The method of claim 1, wherein at least one of said similar number pairs includes a first number and a second number, and wherein said first number can be converted into said second number by adding one or more digits.

6. The method of claim 1, wherein at least one of said similar number pairs includes a first number and a second number, and wherein said first number can be converted into said second number by deleting one or more digits.

7. The method of claim 1, wherein at least one of said similar number pairs includes a first number and a second number, and wherein said first number can be converted into said second number by swapping positions of two or more non-adjacent digits.

8. The method of claim 1, wherein said test chart is printed on paper.

9. The method of claim 1, wherein said test chart is an image on a video display terminal.

10. The method of claim 1, further comprising the steps of measuring and recording the time taken by the individual to compare all number pairs on said test chart with said test chart being printed on paper;
    measuring and recording the time taken by the individual to compare all number pairs on said test chart with said test chart formed by an image on a video display terminal; and
    calculating a ratio of the paper test time to the video test time to determine a video display terminal efficiency value for said individual.

11. A method for measuring visual capacity of an individual in an eye examination comprising the steps of:
    providing a test chart;

positioning an individual at a predetermined observation distance from said test chart;

instructing said individual to examine said test chart and to describe said examination;

recording an accuracy with which said individual describes said test chart;

recording a time taken by said individual to examine said test chart;

and comparing the accuracy and time taken by the individual with predetermined standards for accuracy and time;

said test chart including a plurality of adjacent pairs of multi-digit numbers, with some of said number pairs being the same and others of said number pairs being similar.

12. The method of claim 11 further wherein said individual is instructed to compare each number pair on said test chart to determine whether they are the same.

13. The method of claim 11, wherein said number pairs are formed by a plurality of pairs of adjacent number columns.

14. The method of claim 11, wherein at least one of said similar number pairs includes a first number and a second number, and wherein said first number can be converted into said second number by transposing two adjacent digits.

15. The method of claim 11, wherein at least one of said similar number pairs includes a first number and a second number, and wherein said first number can be converted into said second number by inverting one or more digits.

16. The method of claim 11, wherein at least one of said similar number pairs includes a first number and a second number, and wherein said first number can be converted into said second number by adding one or more digits.

17. The method of claim 11, wherein at least one of said similar number pairs includes a first number and a second number, and wherein said first number can be converted into said second number by deleting one or more digits.

18. The method of claim 11, wherein at least one of said similar number pairs includes a first number and a second number, and wherein said first number can be converted into said second number by swapping positions of two or more non-adjacent digits.

* * * * *